United States Patent [19]

Cooke

[11] 4,112,151

[45] Sep. 5, 1978

[54] IMPREGNATING POROUS ARTICLES

[75] Inventor: Theodore M. Cooke, Kettering, Ohio

[73] Assignee: Monarch Marking Systems, Inc., Dayton, Ohio

[21] Appl. No.: 647,836

[22] Filed: Jan. 9, 1976

[51] Int. Cl.$^2$ ............................ B05D 3/00; B05D 3/12
[52] U.S. Cl. .................................... 427/322; 264/343; 427/244; 427/331
[58] Field of Search ............... 427/322, 331, 336, 243, 427/244, 245, 350, 307; 428/310, 311, 543; 264/343, 78

[56] References Cited

U.S. PATENT DOCUMENTS

| | | | |
|---|---|---|---|
| 2,332,514 | 10/1943 | Holtzclaw | 91/67.8 |
| 2,349,613 | 5/1944 | Chollar | 101/401.1 |
| 2,353,877 | 7/1944 | Chollar | 264/49 |
| 2,427,836 | 9/1947 | Chollar et al. | 101/401.1 |
| 2,432,221 | 12/1947 | Wilson | 260/722 |
| 2,542,527 | 2/1951 | Honey et al. | 264/49 |
| 2,554,483 | 5/1951 | Wilson | 260/2.5 |
| 2,594,348 | 4/1952 | Rockoff | 29/121.8 |
| 2,620,730 | 12/1952 | Gilbert | 101/269 |
| 2,763,208 | 9/1956 | Rockoff et al. | 101/367 |
| 3,062,760 | 11/1962 | Dermody et al. | 264/49 |
| 3,253,542 | 5/1966 | McDonough | 101/367 |
| 3,326,822 | 6/1967 | Albertson | 260/2.5 |
| 3,524,753 | 8/1970 | Sharp | 260/2.5 |
| 3,679,454 | 7/1972 | Penniman | 427/336 |
| 3,920,875 | 11/1975 | Suzuki et al. | 427/336 |
| 3,928,704 | 12/1975 | Heidingsfeld et al. | 428/310 |

OTHER PUBLICATIONS

IBM Technical Disclosure Bulletin, vol. 18, No. 12, May, '76, p. 4074, Edds et al.

*Primary Examiner*—Ronald H. Smith
*Assistant Examiner*—Sadie L. Childs
*Attorney, Agent, or Firm*—Jones, Tullar & Cooper

[57] ABSTRACT

This invention relates to a method of forming pressure expressible composition impregnated, microporous resilient articles. In the process of the invention, a microporous article formed from a solvent swellable resilient organic polymeric material is contacted with a mixture of a pressure expressible composition and a solvent swelling agent, capable of swelling the resilient polymer, and having a volatility greater than that of the pressure expressible compositions, to swell the article and enlarge the micropores. The volatile swelling agent is then removed from the article to provide a microporous article containing the pressure expressible composition within the micropores.

11 Claims, No Drawings

IMPREGNATING POROUS ARTICLES

STATE OF THE ART

Resilient microporous articles containing pressure expressible compositions are shown in the art. Among other uses, these articles are utilized to disperse inks and take the form of pads, rollers or other appropriate shapes. These impregnated articles are highly useful; however, the nature of the microporous structure of the article presents significant problems, in that it is difficult to obtain rapid impregnation of the micropores, and the nature of the pressure expressible composition is limited, in that the presence of particulate material, such as pigments, tends to retard or prevent the proper impregnation of the microporous article.

Examples of impregnated resilient microporous articles impregnatable by the process of the invention can be found in the following U.S. Pat. Nos. 3,253,542; 2,763,208; 2,620,730; 2,432,221; 2,427,836; 2,353,877; 2,332,514, which are hereby incorporated by reference.

DESCRIPTION OF THE INVENTION

This invention relates to a method of forming pressure expressible composition impregnated, microporous resilient articles, and the articles so produced. The process of the ivention is an improved process for impregnating a microporous structure, formed from a resilient solvent swellable organic polymeric material, which comprises mixing the pressure expressible composition with a solvent swelling agent capable of swelling the resilient organic polymer and having a volatility greater than that of the component or components of the pressure expressible composition. The microporous article is contacted with the mixture to swell the article and impregnate the micropores, thereby increasing the size of the micropores and the ease by which impregnation of the micropores is accomplished. The volatile swelling agent is then removed from the article, returning the article to substantially its original size, but containing the pressure expressible composition within the micropores. The pressure expressible composition may be any useful composition which does not significantly attack, or is not significantly attacked by, the resilient organic resilient polymer forming the matrix of the microporous article, including inks, lubricants, odorants, deodorants, medicaments, or other natural or synthetic chemical substances which have utility when continuously or intermittently dispensed in controlled amounts.

The resilient microporous article which can be impregnated by the process of this invention can be formed from a large number of resilient organic polymeric materials. The chemical structure of the polymers is not critical so long as the polymer forms a resilient microporous structure, which is not significantly attacked or degraded by the particular pressure expressible composition contemplated, and so long as the polymer is swellable by a volatile solvent. The organic polymer may be thermosetting or thermoplastic. A preferred polymer is a rubbery like material including natural as well as synthetic rubbers such as the neoprenes, butadiene copolymers, including butadiene acrylonitrile copolymers and butadiene styrene copolymers, polysulfide rubbers, urethane rubbers and rubbery α-monoolefin copolymers such as ethylene, propylene, diene trepolymer rubbers. Other polymers include polymeric compositions such as plastisols formed polyvinyl chloride or vinyl chloride copolymers. Preferably, the resilient microporous article has an apparent hardness below about 50 on a Shore A Durometer.

The microporous structure may be imparted to the polymeric matrix by a number of processes. The precise method of forming the microporous structure is not unduly critical so long as the process provides a relatively uniform microporous interconnecting or open cell void distribution and allows for control of the size of micropores.

The one preferred method of forming a resilient microporous impregnatable article, a dough is produced by incorporating into a rubbery polymeric material, fine particles of a substance which can be removed therefrom and which leave channel like voids or interconnected microvoids in the rubbery polymeric material, and a solvent or dispersant for the rubbery polymer, for example an aromatic solvent or a ketone such as methyl ethyl ketone, which acts to plasticize, soften or disperse the rubbery material, which is readily removable from the rubbery material, and which has no deleterious effect upon said particles. The resultant dough is formed into a block and the solvent removed. If the polymeric material is thermosetting, it is then cured. An article of a desired shape is then machined from the block. The article is treated to remove the particles so as to leave micropores in the rubbery polymers and then dried. The finely divided particles may be any leachable pore forming filler which does not decompose or disintegrate at under the process temperature and conditions used to form and, if necessary, cure the desired shape. Especially useful are inorganic salts such as sodium chloride, sodium sulfate, sodium nitrite, sodium carbonate and sodium bicarbonate. Also useful are soluble organic materials such as sugars and starches. The particles are removed from the desired shape by leaching the filler with a solvent for the filler. Any filler-solvent combination can be used which does not adversely affect the rubber polymer. For various reasons, water is the most desired solvent, although aqueous acids or bases, as well as organic solvents such as alcohols, esters, ethers and aromatics can be employed depending on the materials being treated. The leaching process, especially where water is employed, can be accelerated by the use of hot water, pressure, or the incorporating of wetting agents. The size of the particles of leachable filler is preferably between 20 mesh to about 500 mesh, although the exact desired size of the filler depends upon the desired pore size which in turn is dependent on the type of impregnant and its intended use. A number of such processes are described in U.S. Pat. Nos. 3,253,542; 3,620,730; 2,594,348; 2,554,485; 2,427,836; 2,432,221; 2,353,877 and 2,349,613, which are hereby incorporated by reference. The amount of filler employed is at least that amount necessary to provide interconnecting voids; generally between about 70% to about 95% by weight of the filled article should be filler. The larger the filler particles, the higher the minimum percentage necessary to provide interconnecting voids.

In a similar process, the leachable filled article can be formed from a polymer precursor such as a monomer or mixture of monomers of prepolymers in liquid form which is mixed with filler to produce a paste, slurry, or suspension of such a viscosity to permit it to be formed into a desired shape. The polymerization is then completed by heat, light, radiation, chemical catalyst or other known techniques for the resin system used. A process of this nature is described in U.S. Pat. No. 3,062,760, which is hereby incorporated by reference.

Yet another method of preparing a similar microporous article from a polyvinyl plastisol is described in U.S. Pat. No. 3,253,542, which is hereby incorporated by reference.

Alternatively, other methods of providing microporous structures is by the use of blowing agents to form a foamed structure. One such system is described in U.S. Pat. No. 2,763,208, which is hereby incorporated by reference.

The resultant microporous structure should have sufficient microporosity to absorb an useful pressure expressible quantity of a pressure expressible composition; the pore size being such that the desired composition can be made to enter the pores and be retained therein, while being expressible in response to pressure. The microporous structure should have a degree of resiliency sufficient to allow sufficient compression to express the retained composition under pressure, and to return to substantially its original shape when the pressure is removed. The structure should have some degree of resistance to abrasion and crushing and be able to withstand shock and wear in its intended use. For example, an ink roller should be capable of absorbing a quantity of ink sufficient to make a substantial number of impressions and release ink in response to pressure applied during a printing operation in the required quantity to insure a clearly legible printed impression.

The pressure expressible composition may be any useful composition which has sufficient fluidity to first be impregnated into the micropores and then be dispensed from the micropores by a pressure which resiliently compresses the micropore matrix. The composition should have sufficient viscosity to essentially remain in the micropores absent the application of pressure. A balancing of the pore size, the expressible composition viscosity, the size of any particulate material present in the expressible composition, and the pressure utilized to express the composition will work to provide impregnated articles, containing a wide range of compositions, useful for a wide range of purposes. Examples of pressure expressible compositions which may be utilized include inks, lubricants, medicaments, insecticides, pesticides, odorants, and deodorants, or other functional materials useful in their fluid or vapor state.

The process of the invention is particularly useful in impregnating microporous ink rollers or ink pads. A number of pressure expressible inks are described in U.S. Pat. Nos. 3,467,539; 3,597,244; 3,330,791 and 2,324,671 and are hereby incorporated by reference. A group of inks particularly useful in the process of the invention comprise at least one colorant, that is either a dye or pigment or any combination of two or more thereof, including virtually all of the oil soluble dyes or pigments conventionally employed in the ink art, dispersed in a dispersant.

The vehicle comprises at least one $C_{12}$ and $C_{20}$ carbon atom containing aliphatic monoalcohol containing an even number of carbon atoms, or mixtures thereof, said vehicle having a freezing point less than about 20° C. and preferably less than about 15° C. Preferably, the dispersant comprises oleyl alcohol. Useful aliphatic saturated and olefinically unsaturated fatty alcohols, cetyl alcohol, myristic alcohol, stearyl alcohol, and alcohols derived from linoleic acid and linolenic acid.

The colorants which can be employed include salts of basic azo and amino-azo dyes, such as azo-black, the azine dyes, such as the indulines and the nigrosines, methyl violet base, fuchsin, anthraquinone dyes, and the like, with organic acids, preferably a fatty acid. Pigments, such as carbon black or other insoluble inorganic colorants, may be employed either along or in combination with a dye. Examples of such colorants include chrome yellow, copper phthalocyanine, iron blue and the like.

A presently preferred colorant comprises a nigrosine base colorant admixed with a fatty acid developer. The preferred fatty acid is oleic acid. Other fatty acids include stearic acid, palmitic acid, lauric acid and the like.

Where a fatty acid dye base salt is employed, proportions of the dye base, for example, nigrosine, and fatty acid are selected so that at least a substantial color developing amount of a dye base fatty acid salt is formed, for example, the material known as nigrosine oleate. The amount of fatty acid employed, however, should be no more than, and preferably less than, that amount which forms a non-separating combination or salt with the dye base colorant. Said another way, the amount of fatty acid employed is less than that amount necessary to fully develop the dye base colorant. The use of excess fatty acid above this amount results in a reduction of the sharpness of the image produced upon printing. With nigrosine and similar materials, the exact amount of fatty acid employed varies, in part, on the color intensity desired in the image produced. Typically, a weight of fatty acid about one-half the weight of the nigrosine base color is employed.

The colorant, for example, the above dye base-fatty acid combination, is dispersed in the alcohol vehicle. The alcohol dispersant provides numerous benefits. While substantially non-volatile, therefore, not producing objectionable organic solvent vapors, the vehicle remains a fluid material, which acts as an efficient carrier, through the temperature ranges desirable for use in the transfer elements. Further, for example, the nigrosine base-vehicle mixture is relatively colorless so that the penetration or migration of vehicle from the image formed by the transfer element on a vehicle absorbent image receiving article does not result in a diminution of image sharpness. The amount of alcohol vehicle employed in the ink or image forming mixture is generally at least about 40% by weight of the ink mixture in order to ensure ready expressibility to the ink. Typically, between about 40% and about 90% alcohol vehicle and preferably between about 40% and about 85% by weight of the ink mixture is vehicle.

The solvent swelling agent mixed with the pressure expressible composition can be any "solvent" which will swell the microporous material thereby increasing the pore size by at least about 10%, and preferably about 25%, without dissolving or deteriorating the polymer matrix, which is not deleterious to or capable of forming an aziotrope with the specific pressure expressible composition, and which is more volatile than the pressure expressible composition and will readily volatilize from the polymer matrix allowing the polymer matrix to essentially return to its original size. Examples of organic solvents which swell various resilient polymers include 150° F. naphtha (Solvesso 150), acetone, butyl acetate, polyvinyl pyrolidone (M Pyrol), 2-ethylhexyl acetate, cyclohexanol, methylene chloride, and methyl isobutyl ketone. Examples of organic solvents which swell microporous polyvinyl chloride compositions include materials such as acetone and isopropyl acetate. Water is a suitable solvent swelling agent for some polymer matrixes.

The amount of solvent swelling agent mixed with the pressure expressible composition can be varied widely. Sufficient solvent swelling agent should be present to accomplish the desired degree of swelling. Typically, the ratio of swelling agent to pressure expressible composition ranges between about 10% and about 80% by weight of the pressure expressible composition.

Obviously, the term "solvent swelling agent" is a misnomer of sorts. The swelling agent cannot be a solvent for the polymer matrix, merely a swelling agent, however these materials include materials which are materials commonly marketed or used as solvents.

In the process of the invention, a resilient microporous polymeric article compatible with the intended present expressible composition is prepared by a suitable technique and is then impregnated. A suitable relatively volatile solvent swelling agent is selected which is compatible with the desired pressure expressible composition in an appropriate concentration and the microporous article is contacted with the mixture, preferably by immersion for a time sufficient for the microporous article to swell to at least about 10% and preferably 25% of the original volume, and for the impregnating mixture to enter the microporous structure. While simple contacting is sufficient to accomplish impregnation, the use of heat and/or application of alternating pressure variations, such as intermittent vacuum may reduce the impregnation time. The maximum amount of material impregnatable into the article can be readily determined by calculating the pore volume of the article. If desired, the degree of impregnation can be followed by weight gain, as related to pore volume and the specific gravity of the impregnating material.

The swollen impregnated microporous article is then removed from contact with the impregnating composition and the swelling agent is removed from the article, for example, by ambient evaporation, heat or vacuum. After substantially all the swelling agent has been removed, the article returns substantially to its original size and shape to provide the article having the desired pressure expressible composition retained within the microporous structure. It should be noted that when the pore volume of the article is essentially saturated the article may be slightly larger than its original size, since the resilient material may retain pressure expressible composition in slight excess with regard to the original pore volume.

The following examples illustrate the invention, but the invention is not to be construed as being limited to the details thereof. All parts and percentages in the examples and throughout the specification are by weight, unless otherwise specified.

EXAMPLE 1

A resilient porous roller was formed in the following manner:

A rubber dispersion (20% in an aromatic solvent) was formed from a nitrile rubber compounded inter alia with 50 phr carbon black and a vulcanizing agent (the unsaturated rubber mix had the following cure properties, measured in accordance with ASTM D-2084 at 150° C. at 1° are: $M_H \geq 160$ in-lbs, $t_s(2) < 2$ minutes and $t_c(90) \geq 5$ minutes, the rubber mix showing no reversion of the Rheometer Cure cure, using a 60 minute motor).

80 parts freshly comminuted sodium chloride, passing a 200 mesh screen (U.S. Sieve), was mixed with 20 parts of the above dispersion and the mixture formed into a sheet, the solvent was evaporated from the sheet. The sheet was then chopped into small particles. A quantity of particles were then charged into a mold and formed and cured into a block (320° F., 30 minutes, 500 p.s.i.g). A cylinder (approximately 1½ inch O.D.) was machined from the block, bored and concentrically, adhesively mounted on a steel shaft to form a roller.

The roller was placed in warm flowing water to leach the sodium nitrate from the roller. (The complete removal of sodium nitrate can be monitored by testing the effluent water.) The resultant porous roller was then removed and dried at 140° F. for at least four hours (constant weight).

An ink comprising a 10% dispersion of carbon black in butyl oleate was formed in an Eppenbach homogenizer. 50 parts of the dispersion were mixed with 50 parts of methylene chloride.

The porous roller was immersed in the mixture for 60 minutes. The roller became 50–75% larger in size, being distended and swollen by the methylene chloride.

After the immersion period, the roller was removed from the mixture and placed in a circulating air oven for 2 hours at 60° C., driving off the methylene chloride. When the roller was removed, it had returned to approximately its original size (105% of original volume — the increase caused by retained ink).

The inked roller was employed as the inking roller in a price label printing apparatus.

EXAMPLE 2

A porous roller was prepared, as in Example 1. A lubricating roller was formed by employing as the impregnating mixture a mixture of 5 parts of spindle oil in 25 parts of methylene chloride. The immersion and methylene chloride removal was conducted as in Example 1. The resultant roller is useful as a pressure responsive lubricant metering device.

In a manner similar to the Examples, other porous matrixes, expressible compositions and swelling agents within the scope of the above disclosure may be employed to achieve results within the scope of this invention.

According to the provisions of the patent statutes, there is described above the invention and what are now considered to be its best embodiments. However, within the scope of the appended claims, it is to be understood that the invention can be practiced otherwise than as specifically described.

What is claimed is:

1. A method of forming a resilient microporous article, having a pressure expressible compositon contained in the micropores thereof, which comprises
    (a) contacting a resilient microporous article, containing interconnecting micropores, said article having a matrix comprising a solvent swelling agent swellable resilient organic polymeric material with a mixture comprising:
        (1) a pressure expressible composition and
        (2) a volatile solvent swelling agent, which swells the organic polymeric material forming the matrix, which has a greater volatility than any component of said pressure expressible composition, and which does not form an azeotrope with any component of said pressure expressible composition for a time sufficient to swell the polymeric matrix, enlarge the micropores, and allow said mixture to penetrate into the microporous article and (b) removing the volatile solvent swelling agent to provide a resilient microporous article having said pressure expressible composition contained in its micropores, said composition being expressible upon the application of pressure.

2. A method, as in claim 1, where the pressure expressible composition is an ink composition.

3. A method, as in claim 1, where the pressure expressible composition is a lubricant.

4. A method, as in claim 1, where the polymeric material comprises a natural or synthetic rubber.

5. A method, as in claim 4, where the solvent swelling agent is methylene chloride.

6. A method, as in claim 1, where the microporous article is formed by removing a soluble pore forming particulate filler distributed in a solvent swelling agent swellable polymeric matrix.

7. A method, as in claim 6, where the pressure expressible composition is an ink composition.

8. A method, as in claim 6, where the pressure expressible composition is a lubricant.

9. A method, as in claim 6, where the polymeric material comprises a natural or synthetic rubber.

10. A method, as in claim 9, where the solvent swelling agent is methylene chloride.

11. A method, as in claim 1, of forming a resilient microporous article having a pressure expressible composition contained in the micropores thereof, which comprises (a) forming an article comprising a resilient solvent swelling agent swellable organic polymeric matrix having dispersed therein about 70% to about 95% of the filler article, of a leachable filler, said leachable filler having particle sizes between about 20 mesh and about 500 mesh, (b) removing the leachable filler to provide a microporous article, (c) contacting said microporous article with a mixture comprising:

(1) a pressure expressible composition, and (2) about 10% to about 80% weight of the pressure expressible composition of a volatile solvent swelling agent, which swells the organic polymeric material forming the organic polymeric matrix, which has a greater volatility than any component of said pressure expressible composition, and which does not form an azeotrope with any component of said pressure expressible composition for a time sufficient to swell the micropores at least about 25% and allow said mixture to penetrate into the microporous article and (d) removing the volatile solvent swelling agent, causing said micropores to return substantially to their original size, said micropores containing said pressure expressible composition.

* * * * *